(12) United States Patent
Humphry et al.

(10) Patent No.: US 9,274,024 B2
(45) Date of Patent: Mar. 1, 2016

(54) METHOD AND APPARATUS FOR DETERMINING OBJECT CHARACTERISTICS

(71) Applicant: PHASE FOCUS LIMITED, Sheffield, South Yorkshire (GB)

(72) Inventors: Martin James Humphry, Long Eaton (GB); Kevin Langley, Sheffield (GB); James Russell, Long Eaton (GB); Andrew Michael Maiden, Sheffield (GB)

(73) Assignee: PHASE FOCUS LIMITED, Sheffield, South Yorkshire (GB)

(*) Notice: Subject to any disclaimer, the term of this patent is extended or adjusted under 35 U.S.C. 154(b) by 0 days.

(21) Appl. No.: 14/374,157

(22) PCT Filed: Jan. 24, 2013

(86) PCT No.: PCT/GB2013/050155
§ 371 (c)(1),
(2) Date: Jul. 23, 2014

(87) PCT Pub. No.: WO2013/110941
PCT Pub. Date: Aug. 1, 2013

(65) Prior Publication Data
US 2014/0368812 A1    Dec. 18, 2014

(30) Foreign Application Priority Data
Jan. 24, 2012    (GB) .................................. 1201140.9

(51) Int. Cl.
*G01B 9/00*    (2006.01)
*G01M 11/02*    (2006.01)
(Continued)

(52) U.S. Cl.
CPC ........... *G01M 11/0235* (2013.01); *G01B 11/06* (2013.01); *G01B 11/24* (2013.01); *G01M 11/025* (2013.01); *G01M 11/0228* (2013.01); *G01N 21/41* (2013.01); *G01N 2201/12* (2013.01)

(58) Field of Classification Search
USPC .................................................. 356/124–127
See application file for complete search history.

(56) References Cited

U.S. PATENT DOCUMENTS 6,809,829 B1    10/2004    Takata et al.
6,809,845 B1    10/2004    Kim et al.
(Continued)

FOREIGN PATENT DOCUMENTS

EP    1832930    9/2007
EP    2063260    5/2009
(Continued)

OTHER PUBLICATIONS

Authorized Officer Jamel Derbal, International Search Report dated Feb. 10, 2014 from International Application No. PCT/GB2013/050155 filed Jan. 24, 2013, pp. 1-18.
(Continued)

*Primary Examiner* — Tri T Ton
(74) *Attorney, Agent, or Firm* — MH2 Technology Law Group, LLP

(57) ABSTRACT

Embodiments of the invention provide a method of determining one or more characteristics of a target object, comprising determining a first phase map for at least a region of a target object based on radiation directed toward the target object, determining one or more further phase maps for a sub-region of the region of the target object, determining a number of phase wraps for the sub-region based on a plurality of phase maps for the sub-region, and determining a characteristic of the region of the target object based on the number of phase wraps for sub-region and the first phase map. Embodiments of the invention also relate to a method of determining one or more characteristics of a target object, comprising determining a phase map for at least a region of a target object based on one or more diffraction patterns, determining a wavefront at a plane of the object based upon the phase map, and determining a refractive property of the object based on the wavefront.

19 Claims, 9 Drawing Sheets

(51) Int. Cl.
G01B 11/24 (2006.01)
G01B 11/06 (2006.01)
G01N 21/41 (2006.01)

(56) References Cited

U.S. PATENT DOCUMENTS

| | | | |
|---|---|---|---|
| 7,298,497 B2 * | 11/2007 | Millerd et al. | 356/512 |
| 7,734,084 B2 | 6/2010 | Stewart et al. | |
| 2003/0202634 A1 * | 10/2003 | Gerchberg | 378/147 |
| 2004/0145747 A1 | 7/2004 | Jasapara | |
| 2008/0095312 A1 | 4/2008 | Rodenburg et al. | |
| 2010/0135534 A1 * | 6/2010 | Weston et al. | 382/106 |
| 2010/0165355 A1 | 7/2010 | Kato | |
| 2011/0085173 A1 | 4/2011 | Waller et al. | |
| 2011/0116081 A1 | 5/2011 | Sugimoto | |
| 2011/0134438 A1 | 6/2011 | Kato | |
| 2011/0292379 A1 | 12/2011 | Kato | |
| 2013/0033703 A1 * | 2/2013 | Humphry et al. | 356/73 |
| 2013/0092816 A1 | 4/2013 | Barrett et al. | |
| 2013/0181990 A1 | 7/2013 | Rodenburg et al. | |

FOREIGN PATENT DOCUMENTS

| | | |
|---|---|---|
| EP | 2233905 | 9/2010 |
| GB | 2403616 A | 1/2005 |
| GB | 2481589 | 1/2012 |
| JP | 2005106835 | 4/2005 |
| JP | 2007-534956 A | 11/2007 |
| JP | 2010-204755 A | 9/2010 |
| WO | 96/38722 | 12/1996 |
| WO | 2004/113856 | 12/2004 |
| WO | 2005/106531 | 11/2005 |
| WO | 2005/106531 A1 | 11/2005 |
| WO | 2010/035033 | 4/2010 |
| WO | 2010/064051 | 6/2010 |
| WO | 2010/119278 A1 | 10/2010 |
| WO | 2011/033287 A1 | 3/2011 |
| WO | 2011/131981 | 10/2011 |
| WO | 2011/149000 | 12/2011 |

OTHER PUBLICATIONS

Claus, D. et al. Ptychography: A novel phase retrieval technique, advantages and its application. Proceedings of SPIE, May 21, 2011, vol. 8001, No. 2, pp. 800109-1-800109-6.
Goldstein, Richard M. et al. Satellite radar interferometry: Two-dimensional phase unwrapping. Radio Science, Jul.-Aug. 1988, vol. 23, No. 4, pp. 713-720.
Search Report dated May 30, 2012 from Application No. GB1201140.9, pp. 1-5.
Search Report dated Oct. 3, 2012 from Application No. GB1201140.9, pp. 1-3.
International Preliminary Report on Patentability dated Jun. 13, 2013, International Application No. PCT/GB2011/052392 filed Dec. 2, 2011, pp. 1-7.
International Search Report dated Jun. 13, 2012, International Application No. PCT/GB2011/052392 filed Dec. 2, 2011, pp. 1-5.
Intellectual Property Office Search Report dated Apr. 11, 2011, United Kingdom Application No. GB1020516.9, pp. 1-4.
H. M. L. Faulkner et al., "Error tolerance of an iterative phase retrieval algorithm for movable illumination microscopy", Ultramicroscopy, vol. 103, 2005, pp. 153-164.
Andrew M. Maiden et al., "Superresolution imaging via ptychography", Journal of the Optical Society of America A, vol. 28, No. 4, Apr. 2011, pp. 604-612.
R. W. Gerchberg, "Super-resolution through error energy reduction", Optica ACTA, vol. 21, No. 9, Jan. 1974, pp. 709-720.
Manuel Guizar-Sicairos et al., "Phase retrieval with Fourier-weighted projections", Journal of the Optical Society of America A, vol. 25, No. 3, Mar. 2008, pp. 701-709.
Andrew M. Maiden et al., "An improved ptychographical phase retrieval algorithm for diffractive imaging", Ultramicroscopy, vol. 109, 2009, pp. 1256-1262.
United Kingdom Search Report dated Aug. 11, 2011, Great Britain Application No. GB1107053.9, pp. 1-2.
Martin Dierolf et al., "Coherent laser scanning diffraction microscopy", Journal of Physics: Conference Series, vol. 186, 2009, pp. 1-3.
Andreas Menzel et al., "Advances in Ptychographical Coherent Diffractive Imaging", Proceedings of SPIE, vol. 7076, 2008, pp. 707609-01-707609-08.
Cameron M. Kewish et al., "Ptychographic characterization of the wavefield in the focus of reflective hard X-ray optics", Ultramicroscopy, vol. 110, 2010, pp. 325-329.
Pierre Thibault et al., "Probe retrieval in ptychographic coherent diffractive imaging", Ultramicroscopy, vol. 109, 2009, pp. 338-343.
International Search Report dated Aug. 17, 2012, International Application No. PCT/GB2012/050929 filed Apr. 27, 2012, pp. 1-4.
Manuel Guizar-Sicairos et al., "Phase retrieval with transverse translation diversity: a nonlinear optimization approach", Optics Express, vol. 16, No. 10, 2008, pp. 7264-7278.
Written Opinion of the International Searching Authority dated Oct. 27, 2013, International Application No. PCT/GB2012/050929 filed Apr. 27, 2012, pp. 1-9.
International Preliminary Report on Patentability dated Nov. 4, 2014, International Application No. PCT/GB2013/051168 filed May 3, 2013, pp. 1-8.
International Search Report dated Aug. 5, 2013, International Application No. PCT/GB2013/051168, pp. 1-3.
United Kingdom Search Report dated May 3, 2013, Great Britain Application No. GB1207800.2, pp. 1-7.
Martin Dierolf et al., "Ptychography & Lensless X-Ray Imaging", Europhysics News, vol. 39, No. 1, 2008, pp. 22-24.
Oliver Bunk et al., "Influence of the Overlap Parameter on the Convergence of the Ptychographical Iterative Engine", Ultramicroscopy, vol. 108, 2008, pp. 481-487.
Non-Final Office Action dated Jul. 2, 2015, U.S. Appl. No. 14/114,086, pp. 1-35.
Notification of Reasons for Refusal dated Jun. 11, 2015, Japanese Application No. 2013-541430, pp. 1-4 (including English Language Translation).

* cited by examiner

US 9,274,024 B2

METHOD AND APPARATUS FOR DETERMINING OBJECT CHARACTERISTICS

CROSS-REFERENCE TO RELATED APPLICATIONS

This application is a U.S. National Stage application of PCT/GB2013/050155 filed 24 Jan. 2013, which claims priority to Great Britain Application No. 1201140.9 filed 24 Jan. 2012, the entire disclosures of which are hereby incorporated by reference in their entireties.

Embodiments of the present invention relate to methods and apparatus for determining one or more characteristics of an object.

BACKGROUND

It is often desired to determine one or more characteristics of an object. An example of an object for which it may be desired to determine the characteristics is a contact lens. It is often desired to determine one or more characteristics of the contact lens, such thickness and/or optical power of the contact lens. Thickness measurements are often made using a contact measuring device such as a Rehder-style dial gauge or following an invasive procedure performed on the lens, such as sectioning. However prior art methods often have drawbacks such as a requirement to be performed by a skilled user, and/or the lens to be removed from a native saline environment for measurement.

It is an object of embodiments of the invention to at least mitigate one or more of the problems of the prior art.

SUMMARY OF THE INVENTION

In particular, although not exclusively, embodiments of the present invention relate to methods and apparatus for determining properties of an object including one or more of thickness or refractive power.

The object may be a phase object which is an object which is at least partially transparent and exhibits a phase structure. However embodiments of the invention are applicable to at least partially reflective objects.

BRIEF DESCRIPTION OF THE DRAWINGS

Embodiments of the invention will now be described by way of example only, with reference to the accompanying figures, in which.

DETAILED DESCRIPTION OF EMBODIMENTS OF THE INVENTION

Embodiments of the present invention determine one or more characteristics of an object. Embodiments of the invention will be described with reference to, by way of an example, determining a thickness of an object. However it will be realised that other characteristics of the object may be determined. These other characteristics include refractive index. In a reflection mode of operation, the characteristics include height and/or material variations. Embodiments of the invention are not limited to optical radiation. Embodiments of the invention applicable to other types of radiation may determine magnetic and/or electric fields, sample thickness and mean inner potential (the volume-average of the electrostatic part of a crystal potential).

Embodiments of the invention will be described with reference to determining the characteristics of a lens, such as a contact lens, although it will be realised that the characteristics of other objects may be determined. Such other objects include aqueous materials, gels, hydro-gels and other essentially transparent materials such as gels for use with cells such as CyGEL™ available from Biostatus Ltd.

Figure 1:
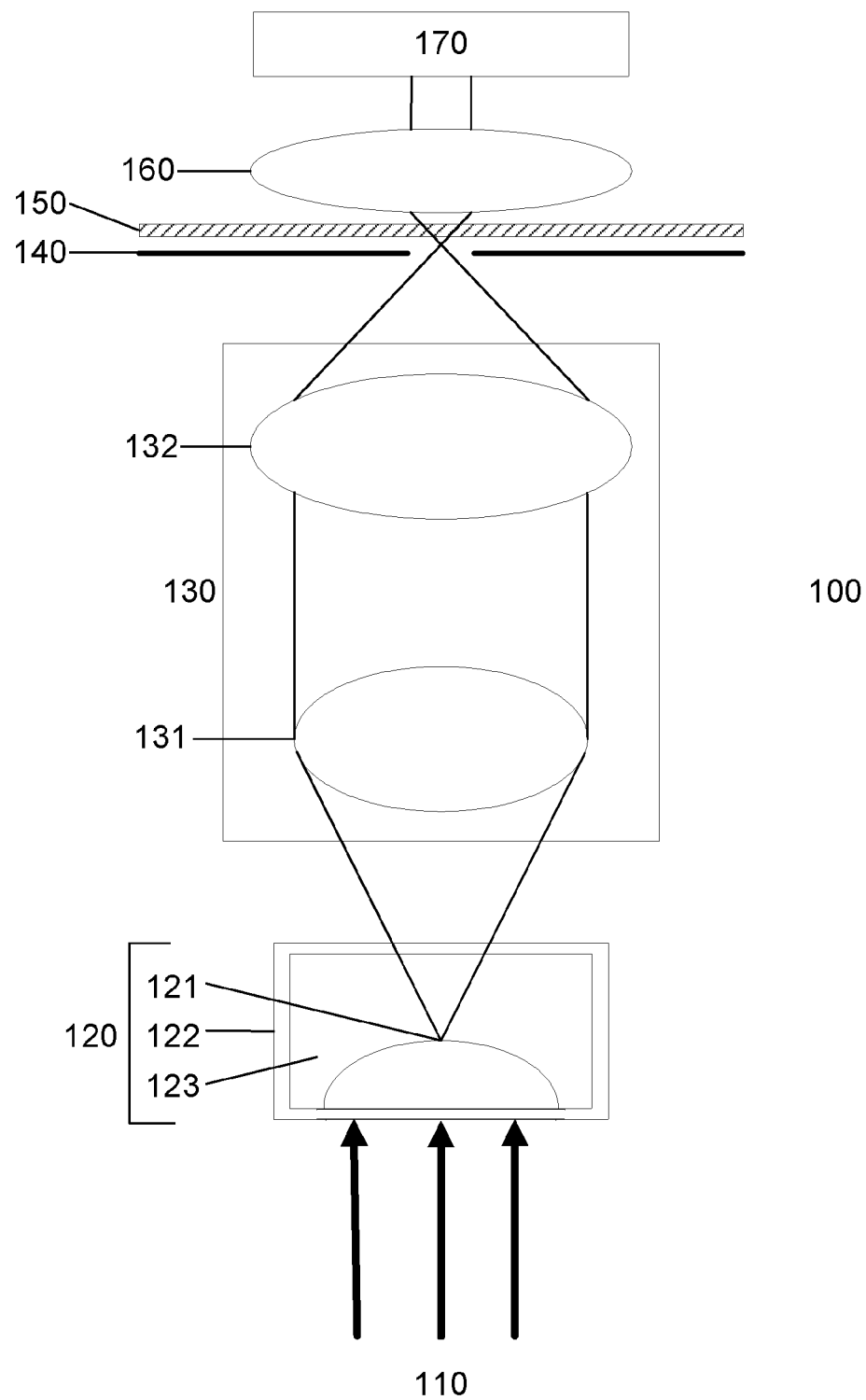
FIG. 1 shows an apparatus according to an embodiment of the invention.

FIG. 1 illustrates an apparatus 100 according to an embodiment of the invention.

The apparatus 100 includes a source (not shown) of radiation 110 which is directed toward an object 120.

In the example shown in FIG. 1, the object 120 comprises a contact lens 121 which is immersed within a saline solution 123 contained within an object holder in the form of a cuvette 122. The object 120 is at least partially transparent in that radiation 110 is able to pass through the object 120. However other apparatus may be envisaged based on FIG. 1 which operate in a reflective mode. Whilst embodiments of the present invention will be described with reference to the object 120 including a contact lens 121 it will be realised that embodiments of the present invention are not restricted in this respect and that embodiments of the invention may be used with any at least partially transparent object to determine one or more characteristics of the object. Embodiments of the invention aim to determine one or more characteristics of the contact lens 121. Advantageously, the characteristics of the lens 121 may be determined whilst the lens 121 is immersed in the saline solution 123.

Although not shown, the object 120 is mounted upon a translation stage capable of moving the object 120 in two dimensions. A microscope 130 (or equivalent optical arrangement) is used to produce a magnified image at an image plane. The microscope comprises an objective lens 131 arranged above the object 120 and a tube lens 132. The objective lens 131 may be exchanged to provide different magnifications and numerical apertures (NA) for the microscope 130, as will be appreciated. An aperture 140 is positioned in the image plane of the apparatus 100. In some embodiments of the invention, the aperture 140 defines a "probe" region for a ptychographic algorithm, as will be explained. A diffuser 150 is arranged immediately downstream of the aperture 140 to decrease a dynamic range of a diffraction pattern measured at a detector 170. The detector 170 may be an array or pixelated detector such as a CCD detector. The diffuser 150 may be arranged as close as is practical to the aperture 140. Downstream of the diffuser 150 an optional auxiliary lens 160 is arranged to reduce the phase curvature of the wavefront at the detector 170 i.e. bring the Fraunhofer plane closer to the aperture 140. The detector 170 is positioned downstream from the auxiliary lens 160 at a known distance from the aperture 140. Preferably the location of the detector 170 is chosen such that it coincides with the Fourier plane of the optical system; however this is not essential for the functioning of the apparatus 100.

The term radiation 110 is understood to be broadly construed as energy from a radiation source. This will include electromagnetic radiation including X-rays, emitted particles such as electrons and/or acoustic waves. Radiation also includes sound waves. In described embodiments, the radiation is light 110 emitted from a light source (not shown) to illuminate the object 120, although it will be realised that embodiments of the invention are not limited in this respect.

Figure 2:
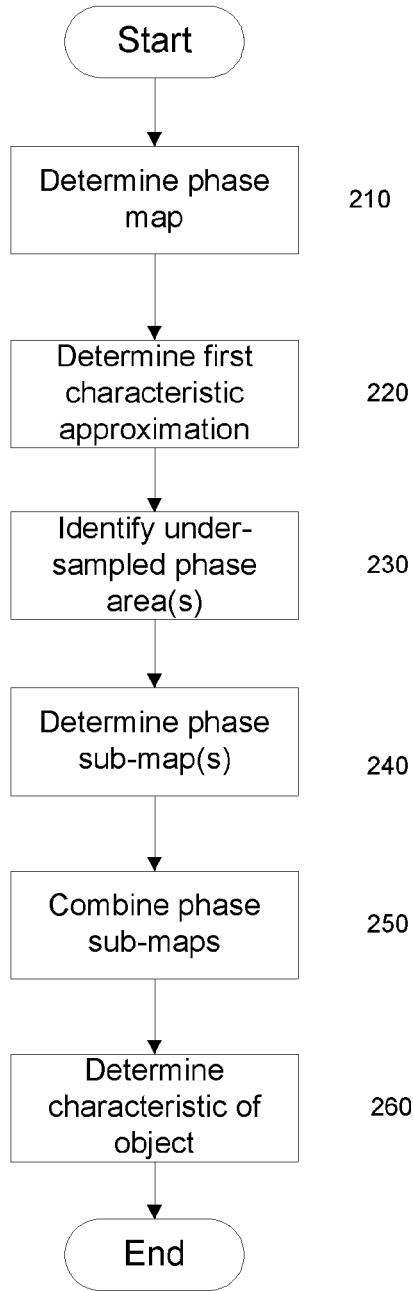
FIG. 2 shows a method according to an embodiment of the invention.

A method 200 according to an embodiment of the invention which may be associated with the apparatus 100 of FIG. 1 is illustrated in FIG. 2.

The method includes a step 210 of determining a phase map over at least a region of the object 120. The phase map indicates a phase shift introduced into the radiation 110 by the object 120 at each of a plurality of spatial locations within the object. The spatial locations may be two-dimensional locations indicated by x, y co-ordinates. Thus $\phi(x,y)$ is a phase shift at the location x, y. It will be appreciated from the use of x, y co-ordinates that the map is a 2D structure, such as a matrix, which stores phase values at a plurality of spatial locations.

The phase map may be produced by a coherent diffractive imaging technique such as a phychographic technique.

WO 2005/106531 by the present Applicant, which is herein incorporated by reference, discloses a method for providing image data which may be used to construct an image of an object based on a measured intensity of a plurality of diffraction patterns. This method is known as a ptychographical iterative engine (PIE). In PIE an iterative phase-retrieval method is used to determine an estimate of the absorption and phase-change caused by the object to a wave field as it passes through or is reflected by the object. This method uses redundancy in the plurality of diffraction patterns to determine the estimate.

WO 2010/064051 by the present Applicant, which is incorporated herein by reference for all purposes, discloses an enhanced PIE (ePIE) method wherein it is not necessary to know or estimate a probe illumination function. Instead a process is disclosed in which the probe function is iteratively calculated step by step with a running estimate of the probe function being utilised to determine running estimates of an object function associated with a target object. It will be realised that other ptychographical methods are known which may also be used.

The present Applicant has also disclosed a characteristic determination method in WO 2011/131981 in which two or more wavelengths of radiation are reflected from a target surface. However this method does not account for "missing wraps", as will be appreciated from the following description.

The apparatus shown in FIG. 1 may be set up as described in the incorporated PIE and/or ePIE references. In order to determine the phase map (a spatial map of the phase shift imparted by the object on transmitted radiation) the object 120 is moved amongst a plurality of positions relative to the radiation 110, aperture 140 and detector 170. In some embodiments, such as that described with reference to FIG. 1, the object 120 is moved upon the translation stage in x and y directions amongst the plurality of positions. However it will be realised that in other embodiments the object 121 may be stationary whilst the radiation 110, aperture 140 and detector 170 are moved relative to the object 120.

As explained in the PIE and ePIE references, an object function O(r) is determined as a result of an iterative process based upon the diffraction patterns measured at the plurality of positions. The object function O(r) represents the phase and amplitude alteration introduced into an incident wave as a result of passing through the object 120 of interest. In the ePIE method, the probe function P(r) may also be determined alongside the object function O(r). By maintaining a fixed positional relationship between the radiation 110, aperture 140 and detector 170 any phase curvature present in the radiation 110 is factored into the probe function P(r) as it is the same at every probe position. In this way, the phase change induced in the radiation by the object 120 may be determined which results in a better approximation of the object function O(r). The object function O(r) may be represented as a two-dimensional matrix wherein each of the matrix positions stores a complex value representing the phase and modulus transfer function of the object 120 at a spatial location of the object 120. Thus the object function O(r) can provide the phase map which indicates the phase change imparted by the object at each spatial location.

In the described example where the object 120 is comprised of one or more additional components such as the cuvette 122, which support or contain the object desired for analysis i.e. the contact lens 121, it may be desired to determine the phase shift imparted by the those additional components, i.e. the cuvette 122, without the lens 121 or saline 123 and to subtract the phase shift imparted by the cuvette 122 as a background measurement. Embodiments of the invention will be described where the phase shift imparted by the cuvette 122 has been removed in this way and further discussion regarding the cuvette 122 will be omitted and the object will be assumed to comprise the lens 121 and saline solution 123.

It has been noted that as the object becomes closer to a pure phase object, i.e. an object which only introduces a change in phase and not in amplitude, such as a lens, particularly where variations only occur at low spatial frequencies, such objects can represent a challenge for ptychographical methods. During the iterative reconstruction process of determining the object function O(r) artificial phase vortices may be introduced which have no physical origin. Once introduced these phase vortices can offer a sufficiently consistent solution to cause the process to stagnate.

Embodiments of the present invention include changes to the PIE and ePIE methods and apparatus referred to above which may minimise this problem.

The auxiliary lens 160 is arranged to cause the detector 170 to be located in, or closer to, the far field Fraunhofer regime rather than the Fresnel regime. Location of the detector 170 in the Fresnel regime may introduce an additional phase curvature in the probe function. An increased likelihood of additional phase vortices exists with the detector 170 located in the Fresnel regime.

In some embodiments of the invention, diffraction patterns measured at respective probe positions are gradually introduced into the iterative method to determine the object function O(r) (the iterative method may also determine the probe function P(r)). The diffraction patterns may be gradually introduced based upon their position with respect to the object 121. In some embodiments, diffraction patterns are introduced generally outward with respect to a centre of the object 121 as the iterative method progresses. The diffraction patterns may be introduced after one or more iterations of the ptychographical method are performed with an initial set of diffraction patterns. Subsequently, further diffraction patterns may be introduced. For example, the initial set of diffraction patterns may be 100 diffraction patterns, although it will be realised that other numbers of diffraction patterns may be considered. The 100 diffraction patterns may be generally centrally located with respect to the object 121. After a predetermined number of iterations have been performed, one or more further diffraction patterns may be introduced. The one or more further diffraction patterns may be generally outwardly located from the initial set of diffraction patterns. After a predetermined further number of iterations, one or more still further diffraction patterns may be introduced, and so on. Eventually, iterations of the method may be performed with all diffraction patterns. It has been observed that the gradual introduction of diffraction patterns in an outwardly progressing manner may reduce a probability of obtaining artificial phase vortices in the reconstruction as the vortices tend to collect at an edge of a central region, thus the vortices are "pushed" outward by the introduction of diffraction patterns in an outwardly expanding manner as reconstruction progresses.

Figure 3:
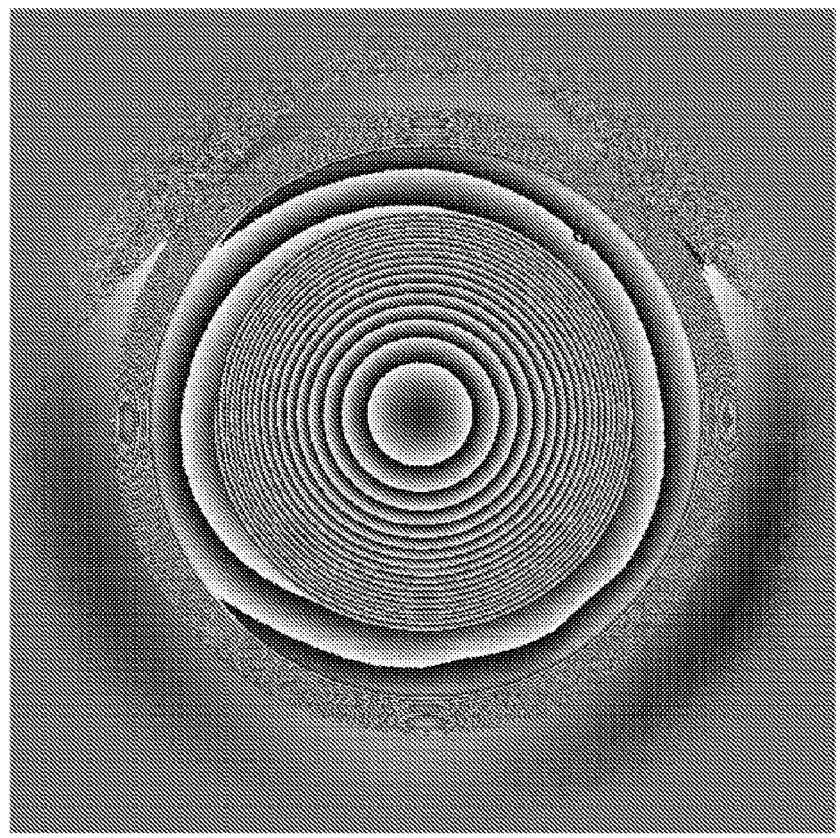
FIG. 3 shows a phase map produced by the method of FIG. 2.

FIG. 3 illustrates a phase map produced by an embodiment of step 210. As noted previously, the phase map is based on the determined object function O(r). The phase map produced in step 210 may be denoted as a low resolution phase map, as will be appreciated from the following description. The low resolution phase map may be determined using a first wavelength of radiation and a microscope having an appropriate NA. The first wavelength may be any wavelength at which the refractive index of the object is known. The first wavelength may be 635 nm. The microscope may have a first NA.

In step 220, a first approximation of one or more characteristics of the object may be determined. Step 220 is a first approximation of the one or more characteristics since, as will be explained, due to possible under-sampling of phase wraps introduced by the object 120, the first approximation may be an underestimate of the characteristic. As noted above, in the described example, the characteristic of the object to be determined is the thickness of the object or lens 121.

Contact lenses are manufactured from materials with well characterised and controlled properties. One material parameter that is particularly carefully controlled is a refractive index of the lens 121, which may be known to 4 significant figures, although this is merely exemplary. When the contact lens 121 is immersed in saline solution 123 the combination will impart a phase shift relative to the phase shift through an equal thickness of saline, $\phi(x, y)$, on light of wavelength $\lambda$ passing through it according to Equation 1

$$\phi(x, y) = \frac{2\pi t(x, y)(n_{lens} - n_{saline})}{\lambda} \qquad \text{Equation 1}$$

Where t(x, y) is the thickness of the contact lens 121 along the optical path at spatial location x, y, and $n_{lens}$ and $n_{saline}$, are refractive indices of the lens 121 and saline solution 123 respectively.

Given known saline and lens refractive indices, the thickness of the lens 121 may be calculated at any point based upon the phase shift at that point according to Equation 2:

$$t(x, y) = \frac{\lambda \phi(x, y)}{2\pi(n_{lens} - n_{saline})} \qquad \text{Equation 2}$$

However, the phase shift determined from the phase map may be a modulo $2\pi$ "wrapped" representation of the phase introduced by the object 121 wherein a phase shift of is indistinguishable from a phase shift of $\phi+2\pi N$ where N is an integer. It may therefore be necessary to unwrap the phase change across the lens 121 to determine the true phase change introduced by the lens 121. The phase may be unwrapped by a suitable algorithm, such as that disclosed by Goldstein et al, Radio Science, 23, 713-720 (1988) which is herein incorporated by reference. Equation 2 now becomes Equation 3:

$$t = \frac{\lambda(\phi + 2\pi N)}{2\pi(n_{lens} - n_{saline})} \qquad \text{Equation 3}$$

where $0<\phi<2\pi$ and N is an integer.

For some objects, particularly objects including at least one region where one or more characteristics of the object, such as thickness, change rapidly the phase map produced by step 210 will be under-sampled. That is, it will not be possible to determine the phase of the radiation in this region as there will be more than one phase wrap per pixel of the detector 170.

In the case of the contact lens 121, the under-sampled region may exist around a periphery or outer edge of the lens 121 where a thickness of the lens 121 rapidly decreases. The missing phase-wraps in this area may lead to an underestimate in the total thickness of the lens 121.

In some embodiments of step 230 prior knowledge of an expected shape of the object 121 may be used to improve the identification of the under-sampled region. In the case of the exemplary contact lens 121, the under-sampled region will be expected to exist around the periphery of the lens 121. The periphery of the lens 121 may be determined by a shape-fitting algorithm. A geometric centre of the lens 121 and a diameter of the lens 121 may be determined from the modulus of the object function. The under-sampled region may be denoted as a dark region present in an image of the modulus, such as a dark ring around the periphery of the lens 121. The dark region is caused by the steep gradient in the thickness of the lens 121 causing light to fall outside of the NA of the apparatus 100 optics. Where the phase gradient G:

$$G > \frac{2\pi NA}{\lambda} \qquad \text{Equation 4}$$

then the region may be under-sampled.

The determination of the centre and diameter may be performed by fitting a shape, such as a circle or ellipse, to the modulus image using a least squares fitting technique.

In some embodiments, the determination of the under-sampled region may be enhanced by Fourier low-pass filtering the complex object function. This may be achieved by truncating a Fourier transform of the complex image and then applying an inverse Fourier transform.

In embodiments where it is desired to display an image of the object 121 the phase map outside of the periphery lens 121, i.e. beyond the dark ring, may be set to 0 in order to eliminate noise outside of the periphery of the lens 121 from the display.

As a result of step 230 one or more regions whose phase is under-sampled are identified. As explained above, for a contact lens 121 the under-sampled region is around the periphery of the lens 121.

To ameliorate the under-sampling problem, in step 240 at least one further phase map is produced. In embodiments of the invention the further phase map is produced for a sub-region of the object. The sub-region at least partially intersects the under-sampled region identified in step 230. However in some embodiments the at least one further phase map may be for cover the whole of the region of the first phase map. The at least one further phase map is determined using radiation having a different wavelength from that used to determine the wavelength in step 210. However, in some embodiments where the further sub-maps are determined at a higher resolution than the phase map determined in step 210, radiation having the same wavelength as used in step 210 may be used to determine one of the further phase maps for the sub-region. It will be realised that one or more further sub-maps may be produced for a plurality of sub-regions of the object 121.

An embodiment of the invention will be described where a plurality of high resolution phase sub-maps are determined for at least some of the under-sampled region 420 using a plurality of different wavelengths of illumination. In some embodiments, two phase sub-maps are determined using two different wavelengths of illumination, although it will be realised that further wavelengths may be used to determine further sub-maps. The sub-maps are considered to be "high resolution" due to their determination using a higher magnification and numerical aperture (NA) detection configuration than the phase map determined in step 210. The high NA arrangement may be achieved by replacing the microscope objective lens 131. In this sense the phase map produced in step 210 is considered to be "low resolution". However it will be realised that the relative resolution of the phase maps is optional i.e. all phase maps may be produced at the same resolution using optics of the same magnification and NA.

Figure 4:
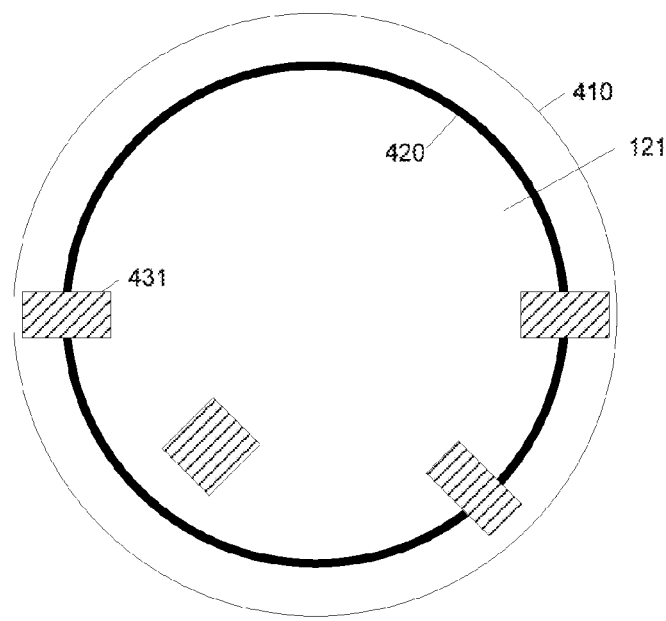
FIG. 4 shows a schematic illustration of an embodiment of the invention.

FIG. 4 illustrates a contact lens 121 in relation to a low resolution region 410 for which the low resolution phase map is determined in step 210, an under-sampled region of under-sampled phase 420 (identified in black) and a region 431 for which at least one high-resolution phase sub-map is produced. It will be realised that the phase sub-map(s) may be produced for one or more i.e. a plurality of regions of the object 121. It will be noted that further regions may be sampled at high resolution using multiple wavelengths, such as those indicated in FIG. 4 without reference numerals. The regions may or may not intersect the under-sampled region 420.

In the exemplary embodiment described two further phase sub-maps will be produced for the region 431. In some embodiments more than two further phase sub-maps are produced for the region 431.

The phase sub-maps 431 are each determined based upon a different radiation wavelength such that they can be combined to eliminate the phase ambiguity for the phase map determined step 210. For a given wavelength $\lambda_1, \lambda_2, \ldots, \lambda_n$ the phase shift introduced by the lens 121 is given by Equations 5a-c:

$$\phi_1 + 2\pi N_1 = \frac{2\pi t(n_{lens} - n_{saline})}{\lambda_1} \quad \text{Eqn. 5a}$$

$$\phi_2 + 2\pi N_2 = \frac{2\pi t(n_{lens} - n_{saline})}{\lambda_2} \quad \text{Eqn. 5b}$$

$$\phi_n + 2\pi N_n = \frac{2\pi t(n_{lens} - n_{saline})}{\lambda_n} \quad \text{Eqn. 5c}$$

Assuming that the saline and lens refractive indices are either known or constant for each wavelength, the above equations form a set of simultaneous equations such that the synthetic thickness $t_s$ may be determined as:

$$t_s = \frac{\lambda_1(\phi_1 + 2\pi N_1)}{2\pi(n_{lens} - n_{saline})} = \frac{\lambda_2(\phi_2 + 2\pi N_2)}{2\pi(n_{lens} - n_{saline})} = \frac{\lambda_n(\phi_n + 2\pi N_n)}{2\pi(n_{lens} - n_{saline})} \quad \text{Eqn. 6}$$

Solving the simultaneous Equation 6 will provide ratios for the various integer $N_n$ values. In most cases, two wavelengths with suitably chosen different wavelengths (e.g. 635 and 675 nm) provide sufficient unambiguous range for contact lens 121 measurement applications. However the wavelengths may be chosen suitable for the object of interest.

For two wavelengths, a synthetic wavelength $\lambda$ can be defined as a solution to Eqn. 6:

$$t_s = \frac{\lambda_s \phi_s}{2\pi(n_{lens} - n_{saline})} \quad \text{Eqn. 7a}$$

Where:

$$\lambda_s = \frac{\lambda_1 \lambda_2}{|\lambda_2 - \lambda_1|} \quad \text{Eqn. 7b}$$

and the synthetic phase $\phi_s$ is given by:

$$\phi_s = \phi_1 - \phi_2 \quad \text{Eqn. 7c}$$

Thus, in some embodiments of step 240 an object function O(r) is determined for region 431 at each of the plurality wavelengths. Based on each of the object functions the high resolution phase sub-maps may be determined for the respective wavelengths.

Figure 5:
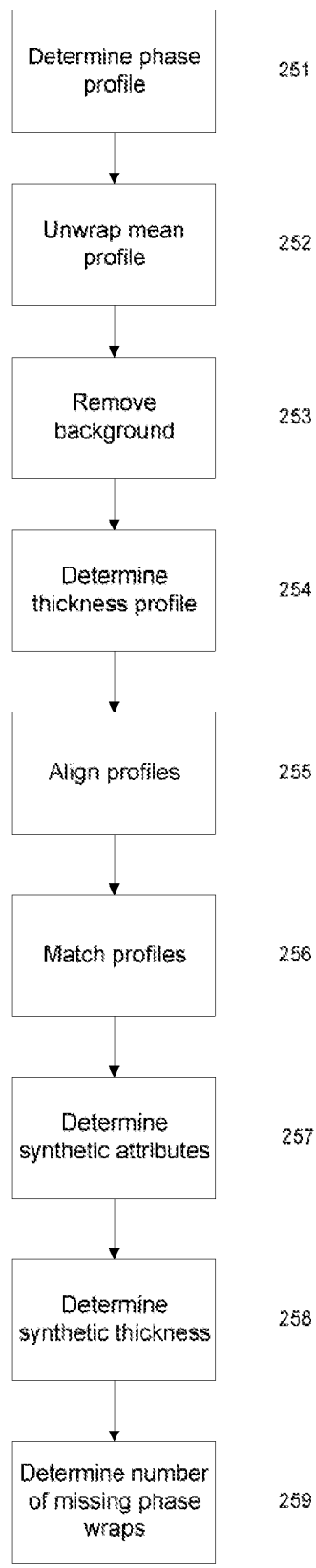
FIG. 5 shows a method according to an embodiment of the invention.

In step 250 the phase sub-maps are combined. Various sub-steps forming step 250 are illustrated in more detail in FIG. 5.

In step 251 a mean phase profile of the lens in the respective region 431 is determined at each wavelength. In this sense, the profile is a one dimensional structure indicating phase against linear distance.

FIG. 6(a) schematically illustrates in plan-view a first region 431 subject to phase sub-mapping in relation to the contact lens' 121 edge.

Figure 6:
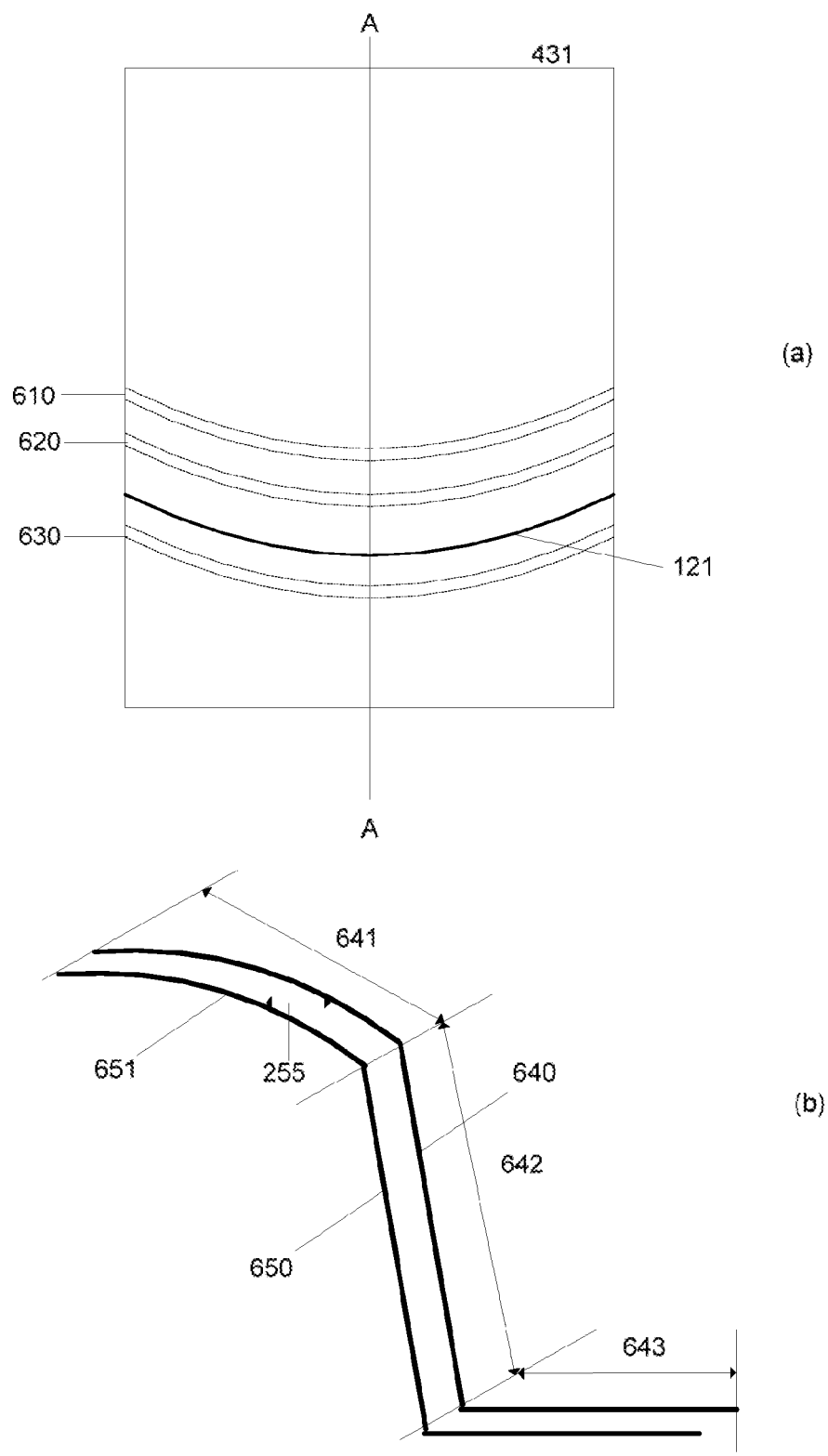
FIG. 6 shows an operation of an embodiment of the invention.

As previously explained, the region 431 may extend across an edge of the lens 121 where a rapid change in lens thickness occurs. Average phase values are determined for spatial locations parallel to the edge of the lens 121. FIG. 6 illustrates with dotted lines first 610 and second 620 rows of phase data points parallel to the lens 121 edge. The phase values in each of the first and second rows 610, 620 are averaged to produce an average phase value at a respective distance from the lens edge 121. Whilst first and second rows 610 620 are shown it is realised that this is merely exemplary and that further average phase values may be determined. In some embodiments, an average phase value may be determined for each row of phase values present in the matrix storing the object function inwardly extending from the edge of the lens 121 i.e. parallel to the line A-A. A mean phase profile for the region 431 is determined at each wavelength.

It will be appreciated that each wavelength will have a different data point spacing as the spacing is a function of radiation wavelength in a ptychographic method.

The mean phase profiles determined in step 251 are unwrapped in step 252. The unwrapping may be performed as previously in step 210.

In step 253 a background phase gradient is removed from each respective phase profile. The phase profile for each wavelength is determined based upon phase values parallel to the lens edge, which may be generally transverse to an elongate orientation of the region 431, any background phase gradient i.e. from outside the lens 121 may affect the mean phase profile. In order to remove the background phase gradient, a region 630 outside of the periphery of the lens 121 is selected. The region 630 may be a row of phase values parallel to the lens 121 edge. A phase gradient for each wavelength is determined by taking a linear fit to the unwrapped phase in the region 630 outside the lens 121 edge. Determining the phase gradient in the region 630 beyond the periphery of the lens 121 is preferable to performing, for example, a background scan of the cuvette 122 as the position at which the phase gradient is determined may vary with the size and shape of the object 121.

In step 254 a thickness profile at each wavelength is determined. The thickness profile is determined based upon the phase profile output from step 253 and Equation 2.

FIG. 6(*b*) illustrates an example schematic thickness profile 640 of the region 431 shown in FIG. 6(*a*) along the line A-A which intersects the lens 121.

As can be appreciated, the thickness profile 640 through the lens 121 shown in FIG. 6(*b*) may be divided into three regions. A first region 641 intersects a generally convex interior portion of the lens 121 within the lens' edge; a second region 642 intersects the edge of the lens 121 wherein the thickness of the lens rapidly decreases; and a third region 643 is external to the lens' edge. It may be assumed that the thickness profile at each wavelength for the first region 641 is consistent since the thickness of the lens' interior does not vary significantly and therefore phase wrapping does not pose a significant problem for this region 641. However for the second region 642 intersecting the edge of the lens 121 where the lens' thickness varies significantly, a number of phase wraps may be missing or underestimated, which would lead to an underestimate in the lens' thickness.

In step 255 the thickness profiles at each wavelength are aligned. In some embodiments of step 255 one of the thickness profiles is selected as a reference profile to which the other thickness profiles are aligned. For example, the thickness profile determined at the first wavelength may be the reference profile, to which the thickness profile determined at the second wavelength is aligned. It will be realised that in some embodiments the thickness profiles at more than one wavelength may be aligned to the reference profile. In order to align the profiles, a region of the reference profile is selected as a reference region. In this exemplary embodiment, the reference region of the lens 121 is chosen to be the first region 641 interior to the lens' edge which is expected to be relatively consistent between all thickness profiles as it contains no undersampled data. However it will be realised that for other objects an appropriate reference region may be selected. The reference region(s) 651 of the at least one further thickness profile(s) 650 at respective different wavelengths are then aligned 255 to the reference region 641 of the reference profile 640. In order to align the profiles 640, 650, the at least one further thickness profile(s) may be shifted laterally i.e. spatially moved and a thickness offset may be added (or subtracted) in order to find a best match to the reference profile. It will be noted that whilst the position values in the at least one further thickness profile(s) 650 may be changed to find the best match to the reference profile, the original phase values at each spatial position or data point are preserved.

In step 256 the plurality of aligned thickness profiles are matched such that a synthetic phase profile may be determined, as explained previously with reference to Equations 7a-7c. In some embodiments of step 256, matching the plurality of thickness profiles may include truncating one or more of the profiles. In this sense, truncating means to remove any data points which extend beyond the range of data points in the other profiles. For example, as a result of the alignment performed in step 255, one or more of the profiles 651 spatially shifted with respect to the reference profile may include data points at positions which extend beyond that of the reference profile 641. These "overhanging" data points may be truncated i.e. removed in step 256 such that all of the profiles have the same spatial range of data points. In some embodiments, step 256 comprises interpolating the data points in one or more profiles such that each profile includes data points at the same spatial positions. As previously explained, the data point spacing in each profile may differ due to the different wavelength for each profile. Therefore the data points in one or more profiles may be interpolated such that each profile has spatially aligned data points. In some embodiments, the data points for the one or more further profiles 651 may be interpolated to match the data point positions of the reference profile 641.

In step 257 synthetic attributes are determined based upon the profiles determined in step 256. In some embodiments, the synthetic attributes are a synthetic phase and synthetic wavelength. As explained previously with reference to Equations 7b and 7c, the synthetic wavelength $\lambda_s$ may be determined between the wavelengths of radiation used for each of the sub-maps and the synthetic phase $\phi_s$ may be determined between the phase values at each spatial location for each of the respective phase profiles.

In step 258 a synthetic thickness $t_s$ of the lens 121 may be determined. The synthetic thickness is determined based upon the synthetic wavelength and phase profile determined in step 257. A synthetic thickness profile may be determined or the synthetic thickness at one or a plurality of points may be determined.

In some embodiments, step 258 contains a validity check to ensure that the determined thickness is valid. Since the thickness gradient at the edge of the lens 121 is relatively steep, and due to the possible presence of noise in the measured data, the determination of thickness based upon the synthetic attributes in step 257 may still result in a missing wrap. The validity check may include comparing the determined thickness against one or more predetermined criteria. The predetermined criteria may be based upon the thickness determined in step 220.

In some embodiments, the synthetic thickness determined in step 258 is checked against the thickness of the lens 121 determined in step 220 to ensure that the synthetic thickness is greater. It will be recalled that for the thickness determined in step 220 the potential problem was missing phase wraps, thus the synthetic thickness should be equal to or greater than the thickness determined in step 220.

In some embodiments, step 258 optionally further includes checking that the synthetic thickness is within a predetermined tolerance of the thickness determined in step 220. In some embodiments, the tolerance is less than $2\pi t$ i.e. one wrap at the synthetic wavelength from the thickness determined in step 220. If the synthetic thickness is greater than one synthetic thickness wrap from the thickness determined in step 220 then the synthetic thickness may be inaccurate.

In step 259 a number of missing phase wraps is determined. Step 259 comprises determining the number of missing wraps for two or more of the phase sub-maps at the different wavelengths. In the example embodiment step 259 comprises determining the number of phase wraps for each of the two wavelength phase profiles. Step 259 comprises determining a number of complete phase wraps for an interior of the lens 121 i.e. for the first region 641. The number of complete phase wraps is compared against the phase profiles at each of the plurality of wavelengths to determine the number of missing wraps comprised in each profile.

In some embodiments, step 259 contains a validity check to ensure that the determined number of missing phase wraps is valid. The consistency check may be advantageous since noise present in the synthetic phase may be comparable to one phase wrap of the wavelength used in step 210.

The validity check in step 259 may comprise comparing the number of missing wraps in each wavelength phase profile. Initially, the number of missing wraps in each phase profile is allowed to vary by ±2 wraps. Any combination of numbers of missing wraps which results in one of the phase maps having a negative number of missing wraps is ignored. For each possible combination of numbers of missing wraps at each wavelength, the calculated thickness values are compared. The combination of values of missing wraps which provides the most consistent thickness value amongst the plurality of wavelengths is selected as the correct number of missing wraps. That is, the combination of missing wraps for the plurality of wavelengths which results in a lowest difference in thickness values amongst the plurality of wavelengths is determined to be the correct number of missing phase wraps.

The determined number of missing phase wraps is added to one of the phase profiles such as the unwrapped reference phase profile to provide an accurate measure of the thickness of the lens 121.

Returning to FIG. 2, step 260 comprises determining a characteristic of the lens 121. In the described example, the characteristic is the thickness of the lens 121. In order to determine the thickness of the lens 121 accurately even in the presence of phase wraps which may lead to an underestimate in the thickness. In step 260 a thickness of a point in the reference phase profile resulting from step 259 is compared against the thickness of the lens 121 determined at the corresponding point in step 220. A difference between the two thicknesses is determined. If phase wraps are missing from the phase map determined in step 210 then the thickness determined in step 220 will be expected to be less than the thickness at the corresponding point of the reference profile. The thickness difference is added to the whole of the lens thickness map determined in step 220 to correct for the underestimate resulting from missing phase wraps. Once the underestimate in thickness difference has been added to the thickness map determined in step 220, this thickness map may be used to determine the thickness of the lens 121 at any point. For example, a representation of the lens 121 thickness may be displayed on a display or the thickness map may be compared against an expected thickness map i.e. based on a design for the lens 121, such that quality a control measure can be implemented.

Figure 7:
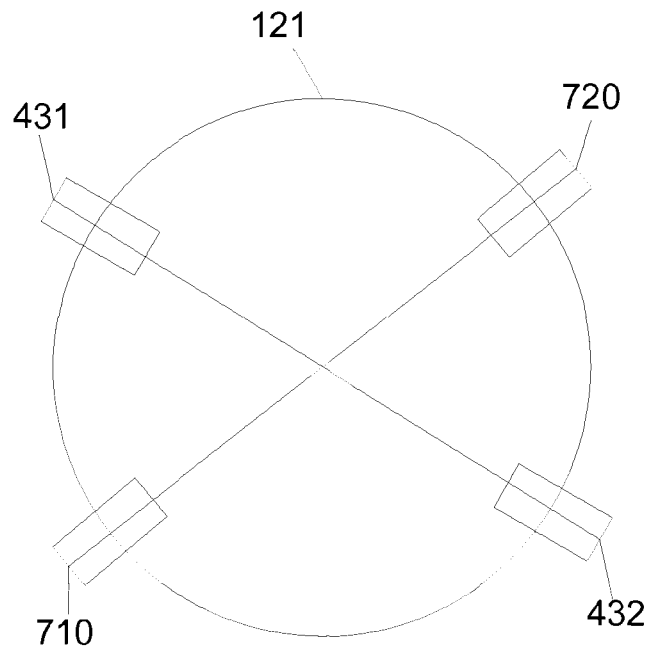
FIG. 7 shows an operation of an embodiment of the invention.
Figure 8:
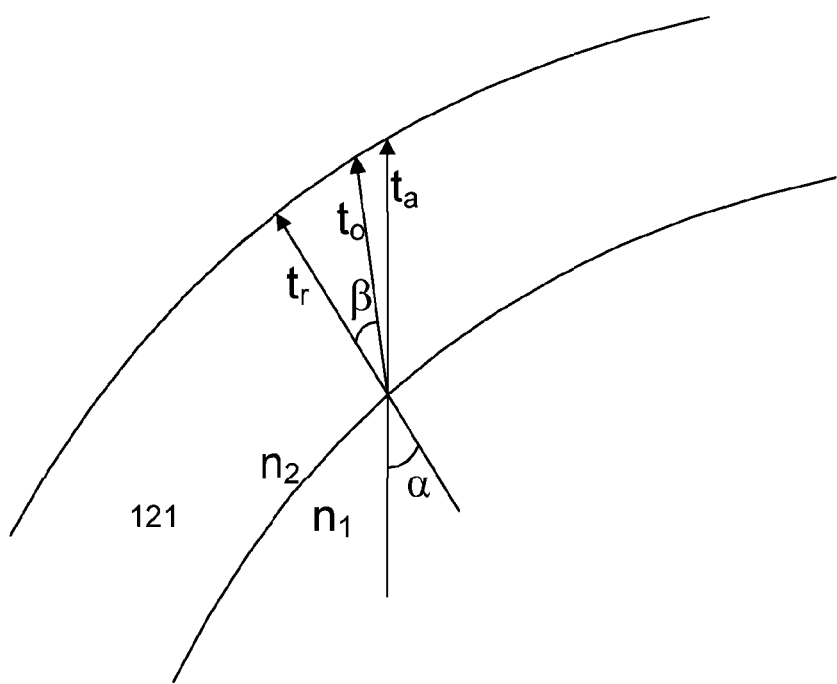
FIG. 8 shows an operation of an embodiment of the invention.

A cross section of an object may be produced by embodiments of the invention from the thickness map produced in step 260. In the case that a phase sub-map has been produced for only one region 431 of the object, such as an edge region of the lens 121, the cross section may be produced in one embodiment by assuming that the opposing edge region has the same profile. However a more accurate cross section may be produced based upon high resolution phase sub-maps 431 of opposing edges, as shown in FIG. 7 and the thickness map resulting from step 260.

It may also be desired to determine a cross section of the object at other radial positions i.e. not interposing the high resolution sub-maps 431, 432. Further cross-sections may be determined using the map produced in step 260.

In order to produce a further cross section of the object 121, a pair of further low resolution sub-maps 710, 720 spanning the region of phase under-sampling i.e. the edge region of the lens 121 are recorded. A location of each of these sub-maps, i.e. with respect to the object 121, is recorded. The phase of each of these sub-maps may be unwrapped as explained previously with reference to step 220 to produce a phase profile of each region 710, 720. Based on the unwrapped phase profiles a thickness profile may be determined based upon Equation 3 for each sub-region 710, 720.

However, as explained previously, due to phase under-sampling the thickness profiles determined for the sub-regions 710, 720 may not be correct. In order to correct for the under-sampling, at least one pixel is identified in each thickness profile for the sub-regions 710, 720. These pixels may be referred to as thickness reference points.

The thickness reference points may be a point furthest inside the lens 121 i.e. closest to the geometric centre, although it will be realised that other points may be chosen. Based upon the location of the thickness reference points, a corresponding pixel is identified in the thickness map determined in step 260 i.e. which has been corrected for phase under-sampling. A difference in thickness may be determined between the pixels in the thickness map from step 260 and each of the sub-region profiles at the thickness reference points. This difference in thickness may be added to each sub-region 710, 720 thickness profile to compensate for the phase under-sampling. The thickness cross section may then be determined based upon the thickness profiles for each sub-region 710, 720 and the profile produced in step 260 by determining thickness values along a line intersecting each sub-region 710, 720. The thickness cross section may be determined at a lower resolution than the data stored in the thickness profiles i.e. not each data point or matrix value along the cross section may be considered. Instead thickness values may be selected from data points at periodic intervals along the cross-section. The data points are selected from a combination of the thickness profiles for each sub region 710, 720 and that determined in step 260.

As explained above, embodiments of the present invention allow the thickness of an object, such as a lens, to be determined. The determined thickness $t_o$ represents the optical thickness of the lens. With a priori knowledge of the shape of the object it is possible to determine other thickness characteristics of the object. For example, in the case of the lens 121 axial or radial thickness of the lens may be determined. The axial or radial thickness of the lens 121 may be determined based upon the optical thickness $t_o$ and a back face curvature value of the lens 121. The back face curvature is a curvature value for the interior face of the lens 121 normally adjacent to the surface of the eye in use. Referring to FIG. 7, the radial thickness $t_r$ is defined as the thickness perpendicular to the back face of the lens 121 and axial thickness $t_o$ is defined as that parallel to the optical axis of the lens 121.

Knowing the base curvature of the lens 121, for any given position on the lens 121 the angle α between the optical axis and the normal to the back (interior) curve can be calculated. Snell's law states: $n_1 \sin(\alpha) = n_2 \sin(\beta)$ where $n_1$ and $n_2$ are the refractive indices of the saline 123 and lens 121 respectively, α is the angle between the incident ray and the normal to the back surface, and β is the angle between the refracted ray and the normal to the back surface. Given the measured optical thickness, $t_o$, geometric estimates for the radial, $t_r$, and axial, $t_a$, thickness are given by Equation 8:

$$t_r = t_o \cos(\beta) \text{ and } t_a = \frac{t_0}{\cos(\alpha - \beta)} \quad \text{Eqn. 8}$$

A further well-defined physical property of a contact lens 121 material is its oxygen permeability, Dk. Since the rate of oxygen transmission to the cornea is critical for the health of the eye, a spatial map of oxygen transmissibility is a crucial measure of a contact lens' clinical performance. Such maps are conventionally displayed as Dk/t where Dk is the oxygen permeability of the lens material, and t is the thickness. Given the value of Dk, such a map is may be calculated from the calculated radial thickness described above.

Embodiments of the present invention determine optical properties of an object such as a lens. The optical properties of the lens may be an optical power of the lens or optical characteristics of the lens such as aberrations of the lens. The aberrations may be expressed in the form of polynomials such as Zernike polynomials. The optical properties may be determined in the form of a map which characterises the optical properties against spatial position for the object. In embodiments of the invention the optical properties may be determined based upon a wavefront position estimated to emanate from the lens based upon a ptychographic method such as PIE or ePIE. As noted above, in some ptychographic methods such as PIE or ePIE an object function for an object is determined based upon a plurality of diffraction patterns recorded at respective different probe locations wherein an object function represents an estimate of the absorption and phase-change caused by the object to a wave field as it passes through or is reflected by the object.

A method according to an embodiment of the invention will now be described with reference to FIG. 9.

In step 910 a phase map for the object, such as the contact lens 121, is determined. The phase map may be produced by an embodiment of step 210 as described with reference to the apparatus shown in FIG. 1. As noted previously, the phase map is based on the determined object function O(r). An example phase map for a contact lens is shown in FIG. 3 as previously discussed.

In step 920 the determined phase map is unwrapped. The unwrapping may be performed as previously explained with reference to step 220 of FIG. 2. The unwrapped phase is determined for each spatial location of the object function O(r). That is, in some embodiments for each position within a two-dimensional matrix used to store the object function. In some embodiments of step 920 the phase map may also be filtered to reduce noise present in the phase map. The filter may be a Hamming Fourier filter, although it will be realised that other filters may be used. It may be useful to filter the phase map since following steps may amplify noise present in the phase map, particularly near a centre of the lens 121.

In step 930 the unwrapped phase map is converted to wavefront position. The unwrapped phase may be converted to wavefront position by Equation 9:

$$\psi = \frac{\phi}{2\pi} \lambda \quad \text{Eqn. 9}$$

Where ψ is the wavefront position and λ is the radiation wavelength used to determine the phase map in step 910 and φ is the unwrapped phase determined in step 920. In step 940 the wavefront is fitted to a sphere. In step 940 only a portion of interest of the wavefront may be fitted to the sphere. The portion may be the portion of the wavefront within an optically active region which, for a contact lens, is a portion within a predetermined radius of a geometric centre of the lens 121. The geometric centre of the lens 121 may be determined by shape-fitting as previously explained. The portion of the wavefront within the predetermined radius is then fitted to the sphere. A centre of the sphere is used to define an optic axis of the lens 121. Advantageously, determining the optic axis in this way based upon the sphere may be more accurate than selecting the geometric centre of the lens 121 as the optic axis. For a contact lens, the radius may be 4 mm although it will be realised that other radii may be chosen appropriately.

In step 950 a phase gradient is determined for each position within the portion of interest. The phase gradient may be determined by fitting a tile of predetermined dimensions to a window of data points surrounding each data point in question. In some embodiments the window is 3×3 data points, although it will be realised that this is merely exemplary. The tile may be fitted to the data points within the window such that the phase gradient may be determined in the x and y axes. The x and y gradients for each data point may then, in some embodiments, be converted to a radial gradient calculated based upon the optic axis determined in step 940. The radial gradient may be calculated by the dot product of the unit vector in the radial direction with the phase gradient vector. The unit vector is determined based upon the location of the point relative to the optic axis and the magnitude of the point.

In step 960 an axial power of the lens 121 is determined. As explained previously with reference to FIG. 1, the lens 121 may be immersed in a solution such as saline 123. Therefore the calculated power may be that in the solution. The axial power may be calculated according to Equation 10:

$$P_{axial} = \frac{1}{r} \frac{\partial z}{\partial r} \quad \text{Eqn. 10}$$

Where $P_{axial}$ is the axial power in the medium, r is the distance from the optical axis and $$\frac{\partial z}{\partial r}$$

is the radial wavefront gradient at that point.

In some embodiments, in order to prevent a spike in the calculated radial power owing to 1/r tending toward infinity toward the optic axis, a power of a region around the optic axis is adjusted. The adjustment may be fitting the wavefront to a sphere, giving a constant power equal to 1/radius of the sphere, or the power of the region can be smoothed.

In step 970 the calculated power in the medium, such as saline, is converted to a power in air.

In a first embodiment of step 970 the power of the lens in air is calculated according to, for example, Optom Vis Sci. 2008 September; 85(9) using Equations 11 and 12:

$$c_1 = \frac{P_{wet} + (n_2 - n_1)c_2}{n_2 - n_1 + \left(\frac{d}{n_2}\right)c_2(n_2 - n_1)^2} \qquad \text{Eqn. 11}$$

$$P_{air} = (n_2 - 1)(c_1 - c_2) + \left(\frac{d}{n_2}\right)c_2(n_2 - n_1)^2 \qquad \text{Eqn. 12}$$

Where $n_1$ is the refractive index of the saline, $n_2$ is the refractive index of the lens, d is the centre thickness and $c_2$ is 1/(lens base curve radius). $P_{wet}$ is the power in the liquid medium, such as saline, and $P_{air}$ is the power in air.

In a second embodiment of step 970 the power in air is calculated based upon a virtual position of the lens in the liquid medium resulting from refraction of light rays at the air-liquid interface.

Figure 10:
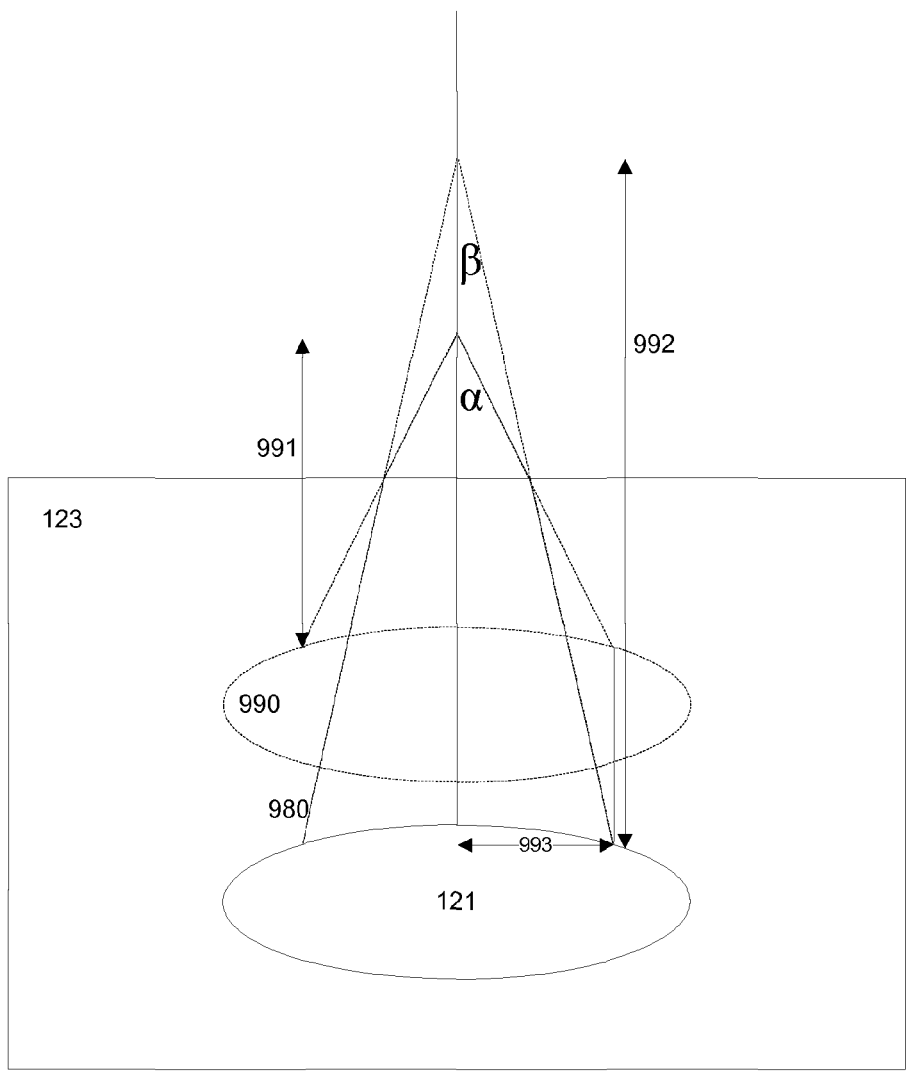
FIG. 10 shows an operation of an embodiment of the invention.

FIG. 10 illustrates a path 980 of light leaving the actual position of the lens 121 in the saline solution 123. As can be appreciated, refraction occurring at the saline-air interface causes a change in the path 980 of light leaving the lens 121. A measured focal length 991 would thus correspond to a virtual lens 990 at a different location to a focal length 992 completely in the saline solution. Based on the differing intersection angles $\alpha$, $\beta$ of the light rays the power of the lens 121 in air may be calculated by Equations 13 and 14 as:

$$\tan(\beta) = \frac{r}{f_{saline}} = rP_{saline} \qquad \text{Eqn. 13}$$

$$\tan(\alpha) = \frac{r}{f_{measured}} = rP_{measured} \qquad \text{Eqn. 14}$$

Where r is a distance between the optical axis and a point on the lens 121, $P_{measured}$ is a measured optical power, $P_{saline}$ is a power in saline solution (or other liquid medium), $f_{measured}$ is a measured focal length and $f_{saline}$ is a focal length in saline (or other liquid medium).

From Snell's Law:

$$n_{saline}\sin(\beta) = \sin(\alpha) \qquad \text{Eqn. 15}$$

Combining these gives Equation 16:

$$P_{saline} = \text{sign}(P_{measured})\left[\left(\frac{n_{saline}}{P_{measured}}\right)^2 + r^2(n_s^2 - 1)\right]^{-1/2} \qquad \text{Eqn. 16}$$

By considering the contact lens as a thick lens, the power in air can then be calculated using Equation 17:

$$P_{air} = \qquad \text{Eqn. 17}$$
$$(n_{lens} - 1)\left[\frac{P_{saline}n_{saline}}{n_{lens} - n_{saline}} + \frac{(n_{lens} - 1)d}{n_{lens}BC}\left(\frac{P_{saline}n_{saline}}{n_{lens} - n_{saline}} + \frac{1}{BC}\right)\right]$$

Where d is the centre thickness of the lens and BC is the back curvature of the lens.

Thus the power of the lens in air may be calculated.

Figure 9:
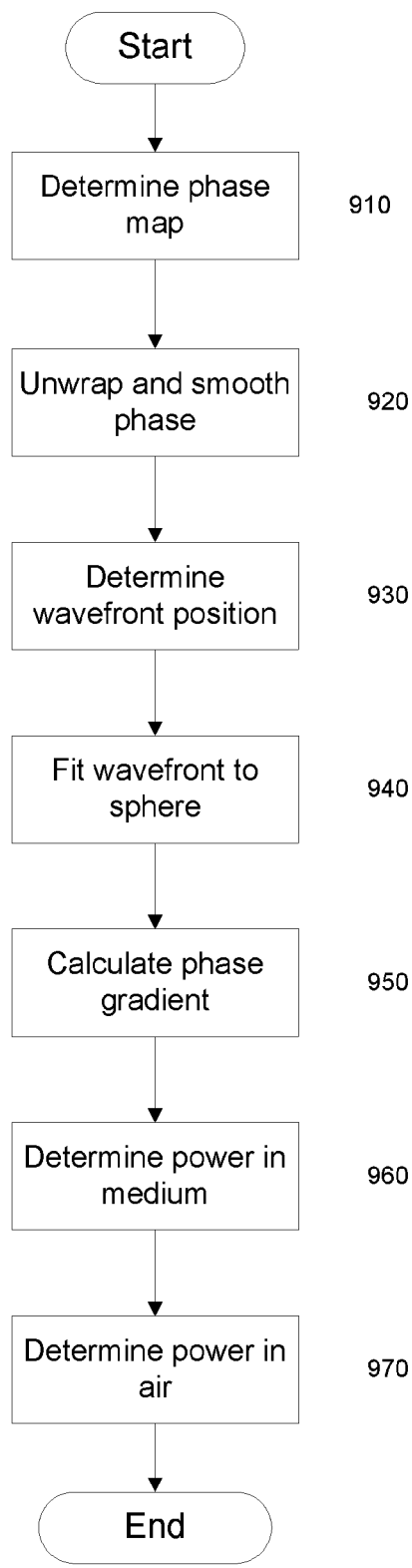
FIG. 9 shows a method according to an embodiment of the invention.

In some embodiments of the invention Zernike polynomials are fitted to the wavefront determined as in step 930 shown in FIG. 9. The Zernike polynomials may characterise aberrations of the lens 121. From the fitted data a clinical prescription power of the lens 121 may also be determined.

In order to determine the Zernike polynomials, the phase map of the lens is determined, the determined phase is unwrapped and may be smoothed, and the wavefront position determined as in steps 910-930 of FIG. 9 and explained above. A portion of the wavefront may then be considered, such as a portion of the wavefront within a predetermined radius of the geometric centre of the lens as previously described with reference to step 940.

The first 15 Zernike polynomials; this is everything from the 0th order (offset) through to the 4th order polynomials. Using Equations 18a and 18b:

$$Z_n^m = R_n^m(\rho)\cos(m\phi) \qquad \text{Eqn. 18a, b}$$
$$Z_n^{-m} = R_n^m(\rho)\sin(m\phi)$$

Where $$R_n^m(\rho) = \qquad \text{Eqn. 19}$$
$$\sqrt{2\frac{n+1}{1+\delta_{m,0}}}\sum_{k=0}^{(n-m)/2}\frac{(-1)^k(n-k)!}{k!\left(\frac{n+m}{2} - k\right)!\left(\frac{n-m}{2} - k\right)!}\rho^{n-2k}$$

Here $\delta_{m,0}$ is the Krönecker delta function such that:

$$\delta_{m,0} = \begin{cases} 1, & \text{if } m = 0 \\ 0, & \text{if } m \neq 0 \end{cases} \qquad \text{Eqn. 20}$$

And $\rho$ is the radial distance from the geometric centre of the lens, normalised such that $\rho=1$ at the edge of the optic region, and, 4), is the azimuthal angle of the position within the image.

Fit the calculated polynomials to the 'cut-out' of the lens from step 940 i.e. the central region using a least squares fitting method.

Use the calculated coefficients to calculate the J45, J0 and M components of the Power vector using Equation 21:

$$J_{45} = -\frac{2\sqrt{6}\, C_2^{-2}}{r_{zone}^2} \qquad \text{Eqn. 21}$$

$$J_0 = -\frac{2\sqrt{6}\, C_2^2}{r_{zone}^2}$$

$$M = \frac{4\sqrt{3}\, C_2^0}{r_{zone}^2}$$

Where, $r_{zone}$, is the radius of the optic zone, and Cnm is the fitted coefficient for the Znm Zernike polynomial.

Convert the [J45 M J0] into the [SphCyl Axis] power format using Equation 22:

$$Cyl = -2\sqrt{J_{45}^2 + J_0^2} \qquad \text{Eqn. 22}$$

$$Sph = M - \frac{Cyl}{2}$$

$$\text{Axis} = \text{abs}\left(\text{atan}\left(\frac{C_1^{-1}}{C_1^1}\right) - \frac{\text{atan}\left(\frac{J_{45}}{J_0}\right)}{2}\right)$$

These then represent the powers of the lens in saline.

In one embodiment, the calculated power in saline from Equation 22 is converted to the power in air using Equation 23:

$$c_1 = \frac{P_{wet} + (n_2 - n_1)c_2}{n_2 - n_1 + \left(\frac{d}{n_2}\right)c_2(n_2 - n_1)^2} \quad \text{Eqn. 23}$$

$$P_{air} = (n_2 - 1)(c_1 - c_2) + \left(\frac{d}{n_2}\right)c_2(n_2 - n_1)^2$$

Where $n_1$ is the refractive index of the saline, $n_2$ is the refractive index of the lens, d is the centre thickness and $c_2$ is 1/(lens base curve radius). $P_{wet}$ is the power in saline and $P_{air}$ is power in air.

However in a further embodiment the power in air can then be calculated using Equation 17 as described above:

$$P_{air} = \quad \text{Eqn. 17}$$
$$(n_{lens} - 1)\left[\frac{P_{saline}n_{saline}}{n_{lens} - n_{saline}} + \frac{(n_{lens} - 1)d}{n_{lens}BC}\left(\frac{P_{saline}n_{saline}}{n_{lens} - n_{saline}} + \frac{1}{BC}\right)\right]$$

Figure 11:
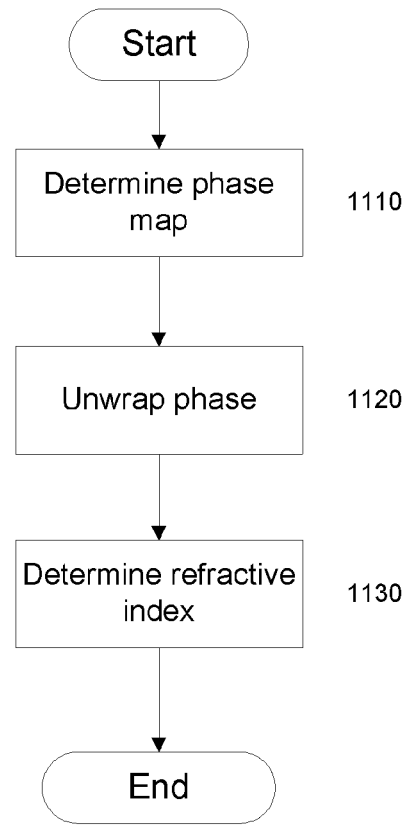
FIG. 11 shows a method according to a further embodiment of the invention.

FIG. 11 illustrates a method of determining a refractive index for an object, such as the contact lens 121. Embodiments of the invention may determine a refractive index map for the object.

The method comprises a step of determining 1110 a phase map for the object. Step 1110 may be performed in the same way as step 910 previously described in connection with FIG. 9.

The method further comprises a step of unwrapping 1120 the phase map for the object. Step 1120 may be performed as previously described step 920. However, unlike in step 920 it may not be necessary to smooth or filter the phase map.

In step 930 a refractive index for the object is determined for at least one position within the object. In some embodiments a refractive index for the object may be determined. Step 930 may be performed based upon two, three or four or more wavelengths of radiation, as will be explained.

As noted above, for a single wavelength of light, the thickness of the contact lens can be determined as:

$$T = \frac{2\pi\phi\lambda}{n_{lens} - n_{saline}} \quad \text{Eqn. 24}$$

In order to make a map of refractive index (RI) n for the object from radiation of a single wavelength, the thickness is required to be known. To overcome this, embodiments of the invention use radiation of multiple wavelengths, thereby allowing relationships to be derived that do not require the thickness of the object to be known as in Equation 25:

$$\frac{n_{lens1} - n_{saline1}}{n_{lens2} - n_{saline2}} = \frac{\phi_1\lambda_1}{\phi_2\lambda_2} \quad \text{Eqn. 25}$$

As will be appreciated, Equation 25 only provides a relationship between the refractive index n at two different wavelengths. In order for this to be useful, an additional relationship is required. A well-known relationship between refractive index and wavelength within the visible spectrum is Cauchy's equation (Cauchy 1836):

$$n(\lambda) = a + \frac{b}{\lambda^2} + \frac{c}{\lambda^4} \quad \text{Eqn. 26}$$

where a, b and c are coefficients. $n_{lens1}$ and $n_{lens2}$ can be replaced in equation 25 with Equation 26 ($n_{saline1}$ and $n_{saline2}$ will be replaced with $n_1$ and $n_2$ for ease) resulting in Equation 27:

$$\frac{a + \frac{b}{\lambda_1^2} + \frac{c}{\lambda_1^4} - n_1}{a + \frac{b}{\lambda_2^2} + \frac{c}{\lambda_2^4} - n_2} = \frac{\phi_1\lambda_1}{\phi_2\lambda_2} \quad \text{Eqn. 27}$$

which can be rearranged to give:

$$a(\phi_2\lambda_2^5\lambda_1^4 - \phi_1\lambda_1^5\lambda_2^4) + b(\phi_2\lambda_2^5\lambda_1^2 - \phi_1\lambda_1^5\lambda_2^2) + \quad \text{Eqn. 28}$$
$$c(\phi_2\lambda_2^5 - \phi_1\lambda_1^5) + (\phi_1\lambda_1^5\lambda_2^4 n_2 - \phi_2\lambda_2^5\lambda_1^4 n_1) = 0$$

A third wavelength can be introduced to provide two similar equations giving a comparison with the third wavelength and each of the two wavelengths already used, as in Equations 29 and 30:

$$a(\phi_3\lambda_3^5\lambda_1^4 - \phi_1\lambda_1^5\lambda_3^4) + b(\phi_3\lambda_3^5\lambda_1^2 - \phi_1\lambda_1^5\lambda_3^2) + \quad \text{Eqn. 29}$$
$$c(\phi_3\lambda_3^5 - \phi_1\lambda_1^5) + (\phi_1\lambda_1^5\lambda_3^4 n_3 - \phi_3\lambda_3^5\lambda_1^4 n_1) = 0$$

$$a(\phi_2\lambda_2^5\lambda_3^4 - \phi_3\lambda_3^5\lambda_2^4) + b(\phi_2\lambda_2^5\lambda_3^2 - \phi_3\lambda_3^5\lambda_2^2) + \quad \text{Eqn. 30}$$
$$c(\phi_2\lambda_2^5 - \phi_3\lambda_3^5) + (\phi_3\lambda_3^5\lambda_2^4 n_2 - \phi_2\lambda_2^5\lambda_3^4 n_3) = 0$$

As the only unknowns in Equations 28-30 are the coefficients a, b and c, these three equations can be solved simultaneously to determine the values of the coefficients a, b and c. A map of the value of each of these coefficients may be determined which can then be used, in conjunction with Equation 26, to create a map of the RI of the contact lens at any wavelength of radiation.

The radiation used in step 1130 may be visible radiation or may include radiation in the invisible spectrum such as infrared or ultraviolet radiation. Although the Cauchy equation is most accurate at visible wavelengths, those skilled in the art will appreciate that an alternative dispersion fit could be used for alternative wavelengths, such as the Sellmeier equation. It will also be appreciated that the above teaching may be extended to utilise more than three wavelengths of radiation. Embodiments of the invention may utilise two or more wavelengths, three wavelengths as described above, or at least four wavelengths of radiation.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A method of determining one or more characteristics of a target object, comprising:
    determining a first phase map for at least a region of a target object based on radiation directed toward the target object;
    determining one or more further phase maps with a higher resolution than the first phase map for a sub-region of the region of the target object;
    determining a number of phase wraps for the sub-region based on the one or more further phase maps for the sub-region; and
    determining a characteristic of the region of the target object based on the number of phase wraps for the sub-region and the first phase map.

2. The method of claim 1, wherein the radiation directed toward the target object has a first wavelength, at least some of the further phase maps being based on radiation directed toward the target object having a wavelength different from the first wavelength.

3. The method of claim 1, wherein the one or more further phase maps for the sub-region are based on radiation measured at a detector having a higher resolution than for the first phase map.

4. The method of claim 1, wherein the one or more further phase maps are measured at a detector having an optical arrangement with a higher numerical aperture (NA) than for the first phase map.

5. The method of claim 1, comprising determining a characteristic of the object in the sub-region based on the plurality of the phase maps.

6. The method of claim 1, wherein the step of determining one or more further phase maps for the sub-region of the region of the target object comprises determining a plurality of further phase maps for the sub-region.

7. The method of claim 1, wherein the characteristic of the sub-region is determined based upon a synthetic phase change.

8. The method of claim 1, comprising determining an average characteristic for the sub-region based upon the plurality of phase maps for the sub-region.

9. The method of claim 5, comprising determining a number of phase wraps for each of the plurality of further phase maps.

10. The method of claim 6, wherein the number of phase wraps for the sub-region is determined based upon the number of phase wraps for each phase map for the sub-region and one or more predetermined criteria.

11. The method of claim 1, comprising determining a background characteristic based upon the plurality of phase maps.

12. The method of claim 8, wherein a portion of the plurality of phase maps extend beyond a periphery of the object and the background characteristic is determined based the portion.

13. The method of claim 7, wherein the average characteristic is determined based upon characteristics of a plurality of points within the sub region.

14. The method of claim 1, comprising determining a characteristic profile of the sub-region.

15. The method of claim 13 wherein the characteristic profile of the sub-region is determining for each of the plurality of phase maps for the sub-region.

16. The method of claim 1, wherein the first and further phase maps are determined based on a coherent diffractive imaging (CDI) process.

17. The method of claim 15, wherein the CDI process is based upon a plurality of diffraction patterns at respective probe locations.

18. An apparatus, comprising:
    one or more memory devices storing instructions; and
    one or more processors coupled to the one or more memory devices and configured to execute the instructions to perform a method comprising:
    determining a first phase map for at least a region of a target object based on radiation directed toward a target object;
    determining one or more further phase maps with a higher resolution than the first phase map for a sub-region of the region of the target object
    determining a number of phase wraps for the sub-region based on the one or more further phase maps for the sub region; and
    a characteristic of the region of the target object based on the number of phase wraps for sub-region and the first phase map.

19. A non-transitory computer readable medium comprising instructions that cause a processor to perform a method comprising:
    determining a first phase map for at least a region of a target object based on radiation directed toward a target object;
    determining one or more further phase maps with a higher resolution than the first phase map for a sub-region of the region of the target object;
    determining a number of phrase wraps for the sub-region based on the one or more further phase maps for the sub-region; and
    determining a characteristic of the region of the target object based on the number of phase wraps for sub-region and the first phase map.

* * * * *